United States Patent
Düppre

(10) Patent No.: US 9,869,642 B2
(45) Date of Patent: Jan. 16, 2018

(54) METHOD FOR X-RAYING PRODUCTS

(71) Applicant: Wipotec Wiege- und Positioniersysteme GmbH, Kaiserslautern (DE)

(72) Inventor: Theo Düppre, Kaiserslautern (DE)

(73) Assignee: Wipotec GmbH, Kaiserslautern (DE)

( * ) Notice: Subject to any disclaimer, the term of this patent is extended or adjusted under 35 U.S.C. 154(b) by 690 days.

(21) Appl. No.: 14/032,941

(22) Filed: Sep. 20, 2013

(65) Prior Publication Data

US 2014/0170274 A1 Jun. 19, 2014

(30) Foreign Application Priority Data

Sep. 21, 2012 (EP) .................... 12401189

(51) Int. Cl.
*G01N 23/02* (2006.01)
*G01N 23/083* (2006.01)

(52) U.S. Cl.
CPC ........... *G01N 23/02* (2013.01); *G01N 23/083* (2013.01); *G01N 2223/618* (2013.01); *G01N 2223/643* (2013.01); *G01N 2223/652* (2013.01)

(58) Field of Classification Search
CPC ................ G01N 23/02; G01N 23/083; G01N 2001/024; G01N 2223/618; G01N 2223/643; G01N 2223/652; G01V 5/0016
See application file for complete search history.

(56) References Cited

U.S. PATENT DOCUMENTS

| 4,901,861 | A | 2/1990 | Cicchelli |
| 5,428,657 | A | 6/1995 | Papanicolopoulos et al. |
| 5,629,966 | A | 5/1997 | Dykster et al. |
| 6,492,645 | B1* | 12/2002 | Allen ............. A23L 3/263 250/453.11 |
| 6,520,311 | B1 | 2/2003 | Maeda |
| 2003/0019717 | A1* | 1/2003 | Maeda ............. B07C 5/02 198/339.1 |
| 2004/0105797 | A1* | 6/2004 | Camu ............. A23L 3/001 422/304 |
| 2005/0077472 | A1* | 4/2005 | Korenev ............. G01N 23/06 250/360.1 |

(Continued)

FOREIGN PATENT DOCUMENTS

| DE | 102009051643 A1 | 5/2011 |
| DE | 102005010183 B4 | 2/2012 |

(Continued)

OTHER PUBLICATIONS

Machine Translation of JP2009168590A.*

(Continued)

*Primary Examiner* — Glen Kao
(74) *Attorney, Agent, or Firm* — The Culbertson Group, P.C.

(57) ABSTRACT

A method for X-raying products of a product stream in which products are conveyed in a conveyance direction before the X-raying in a number n lanes parallel to each other. Several adjacent products transverse to the conveyance direction are transferred as a group together into a radiation-protected X-ray room, and the products are rearranged for an X-ray process in the X-ray room such that the shadowing effects during the X-ray process are reduced.

18 Claims, 12 Drawing Sheets

(56) References Cited

U.S. PATENT DOCUMENTS

| | | | | |
|---|---|---|---|---|
| 2007/0230656 A1* | 10/2007 | Lowes | ................... | B64F 1/368 378/57 |
| 2010/0232570 A1* | 9/2010 | Duppre | ................. | B65B 57/10 378/57 |
| 2011/0142201 A1* | 6/2011 | Eberhard | ............. | G01V 5/0008 378/57 |

FOREIGN PATENT DOCUMENTS

| | | | | |
|---|---|---|---|---|
| EP | 1279950 A1 | 1/2003 | | |
| JP | H9-127017 | 5/1997 | | |
| JP | 2001225029 A1 * | 8/2001 | ............... | B07C 5/02 |
| JP | 2003139723 A * | 5/2003 | | |
| JP | 2004125673 A | 4/2004 | | |
| JP | 2009168590 | 7/2009 | | |
| JP | 2009168590 A1 * | 7/2009 | ............. | G01N 23/04 |
| JP | 2009294092 A | 12/2009 | | |
| JP | 2010139425 A | 6/2010 | | |
| JP | 2011-232120 | 11/2011 | | |
| WO | 9613340 A1 | 5/1996 | | |

OTHER PUBLICATIONS

Machine Translation of JP2001225029A.*
EPO, Extended European Search Report dated Mar. 5, 2013 in corresponding European patent application No. 12401189.1 (7 pages)
JPO, Notification of Reasons for Refusal dated Aug. 18, 2014 in corresponding Japanese Patent Application No. 2013-196972 (6 pages).
JPO, Notification of Reasons for Refusal dated Mar. 16, 2016 in corresponding Japanese Patent Application No. 2015-117747 (6 pages).

* cited by examiner

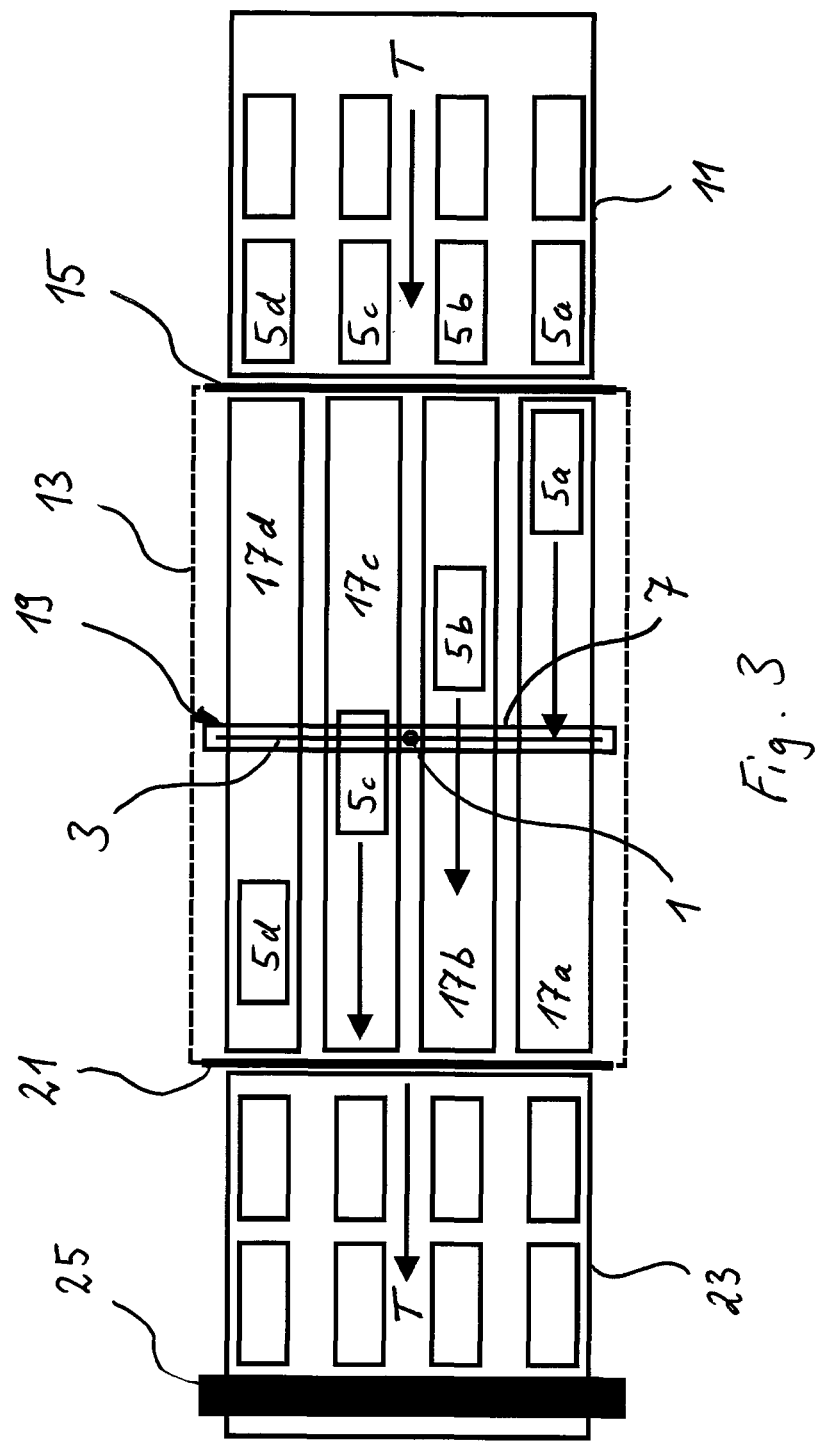

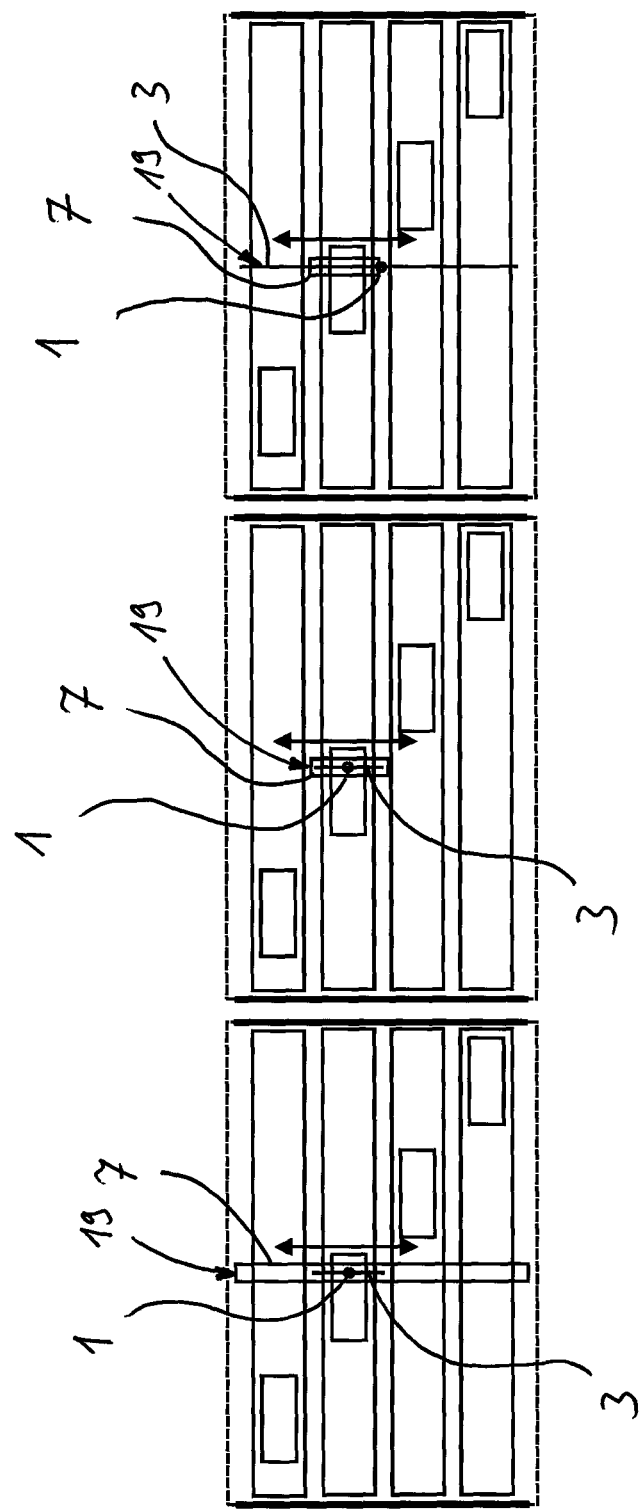

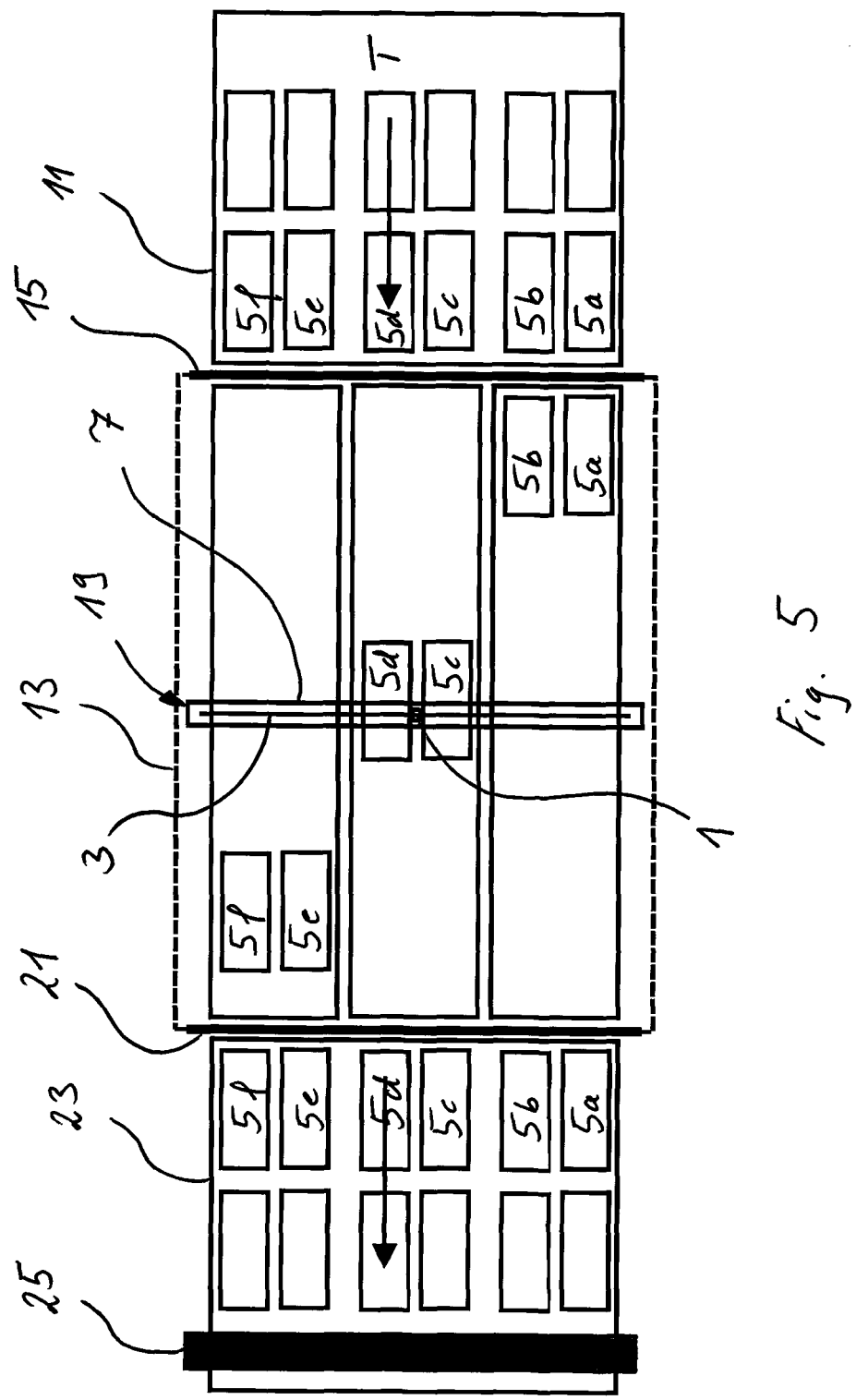

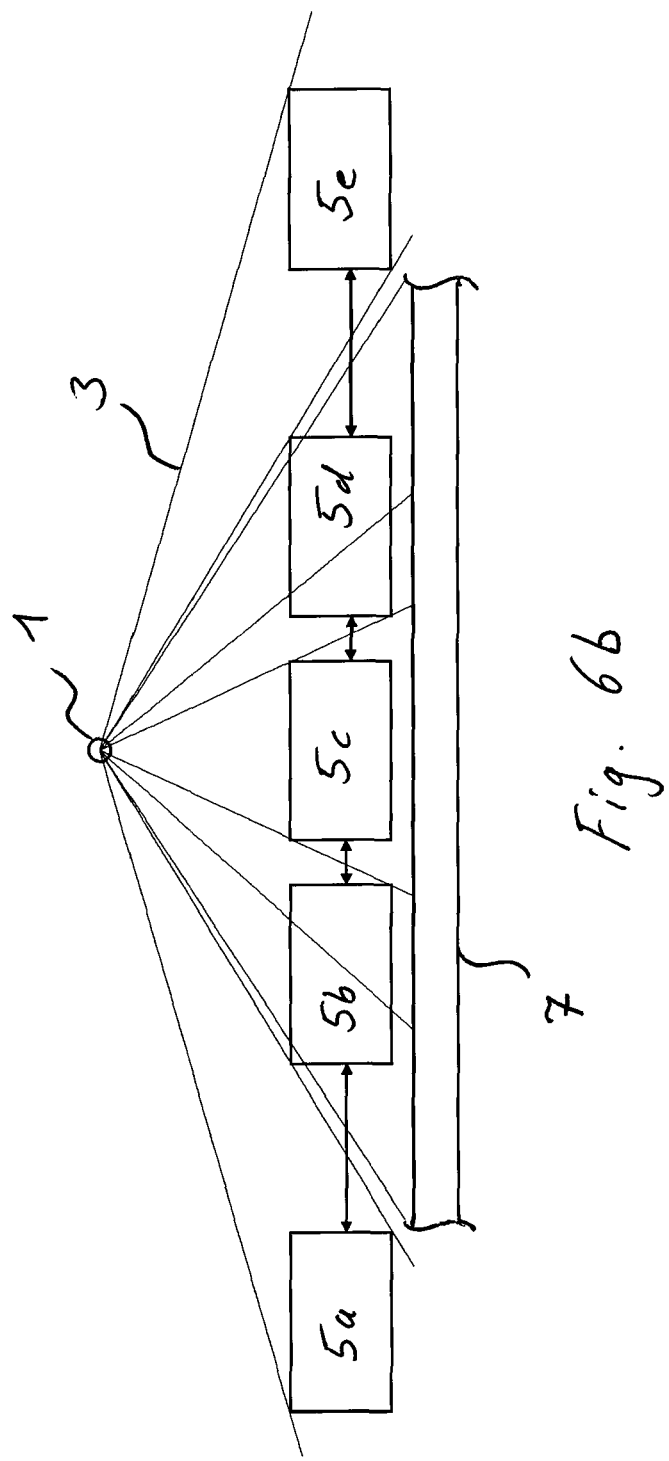

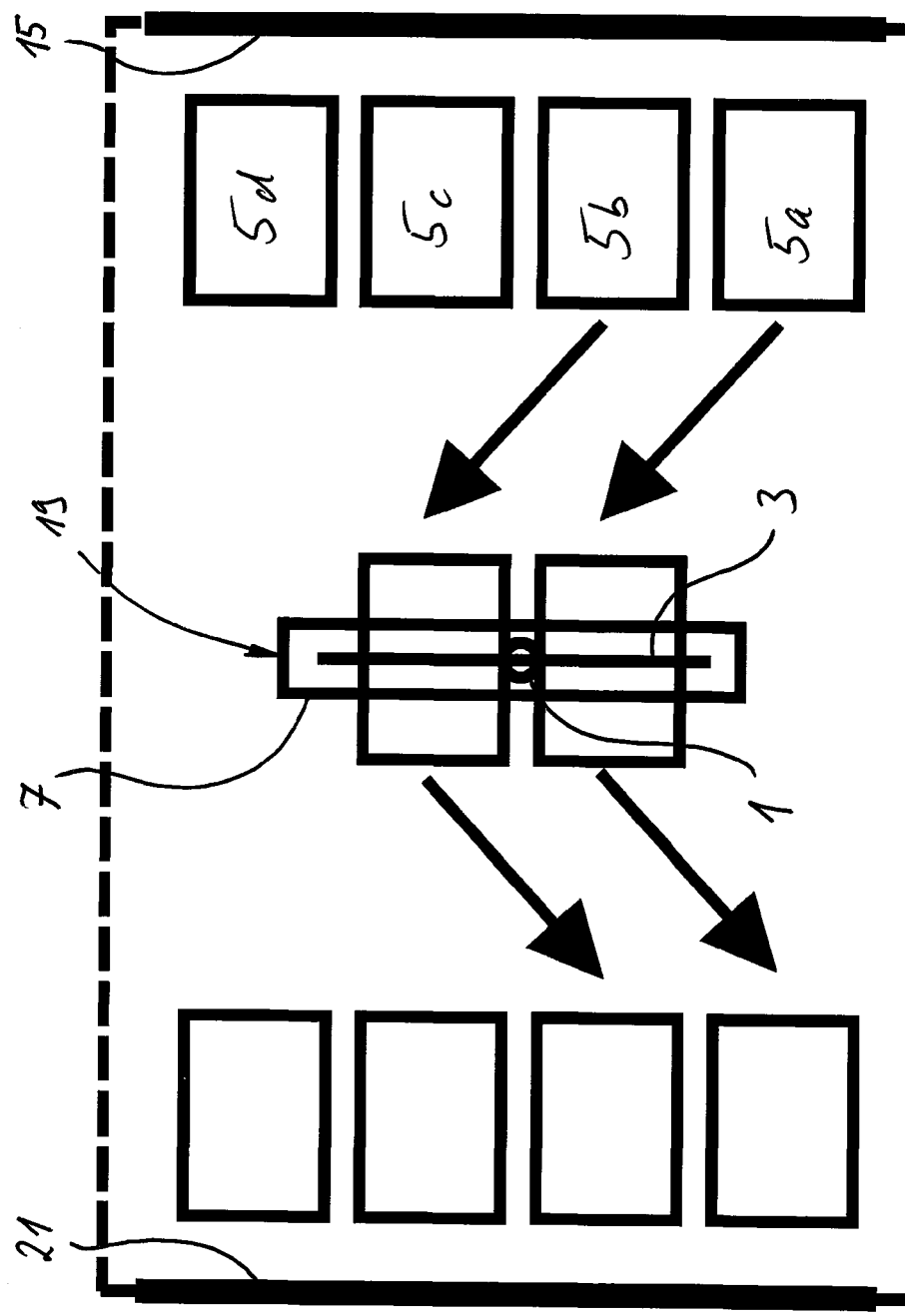

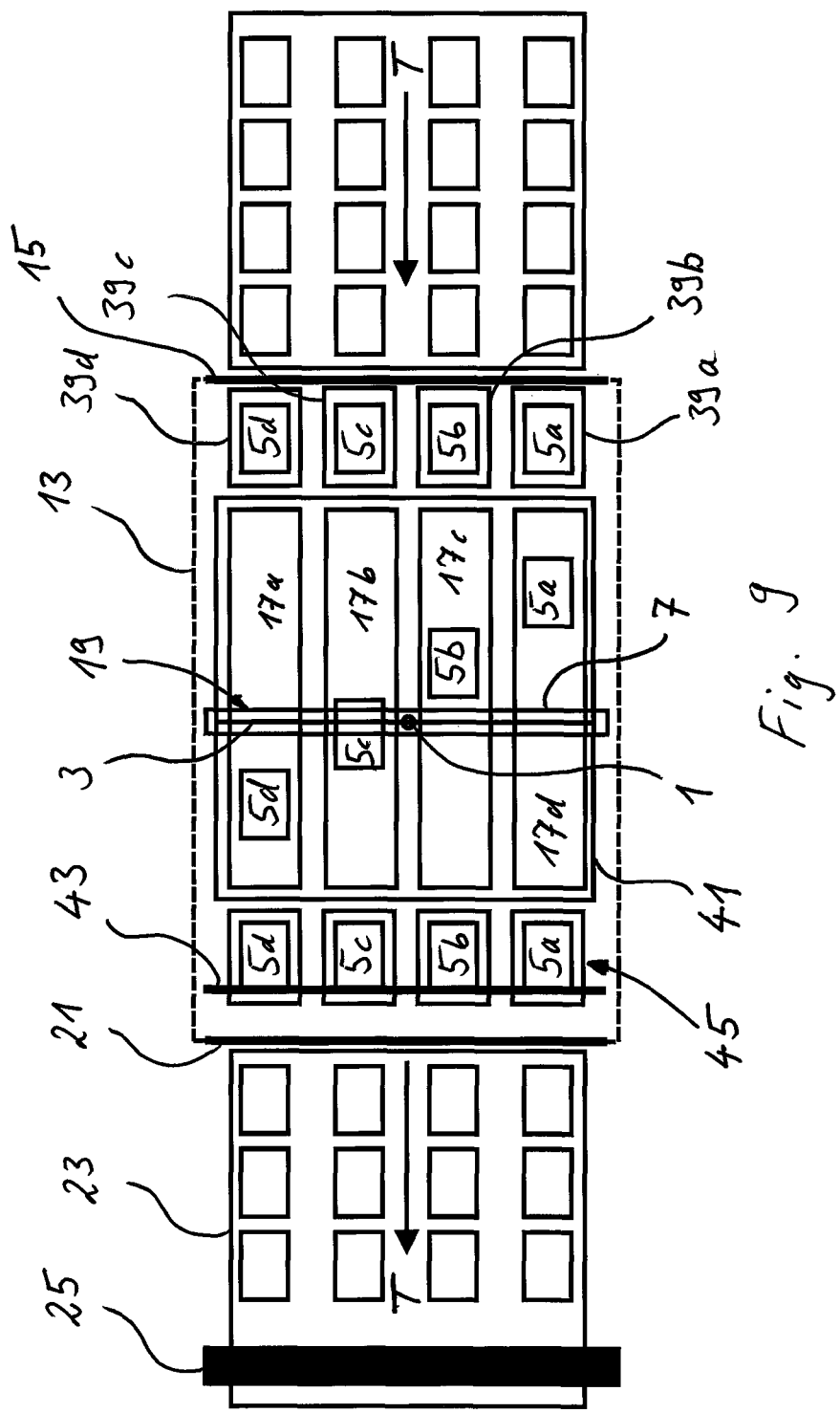

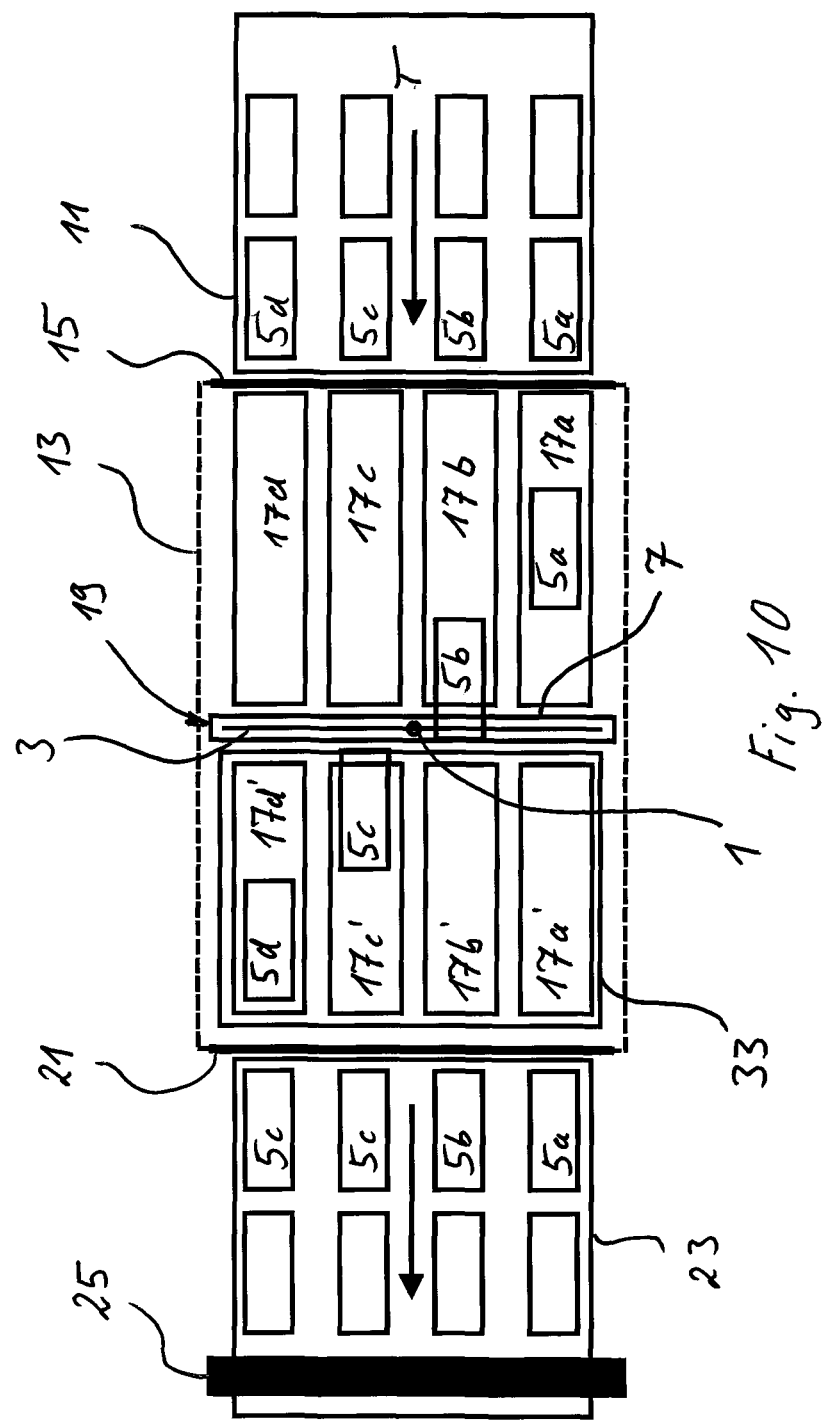

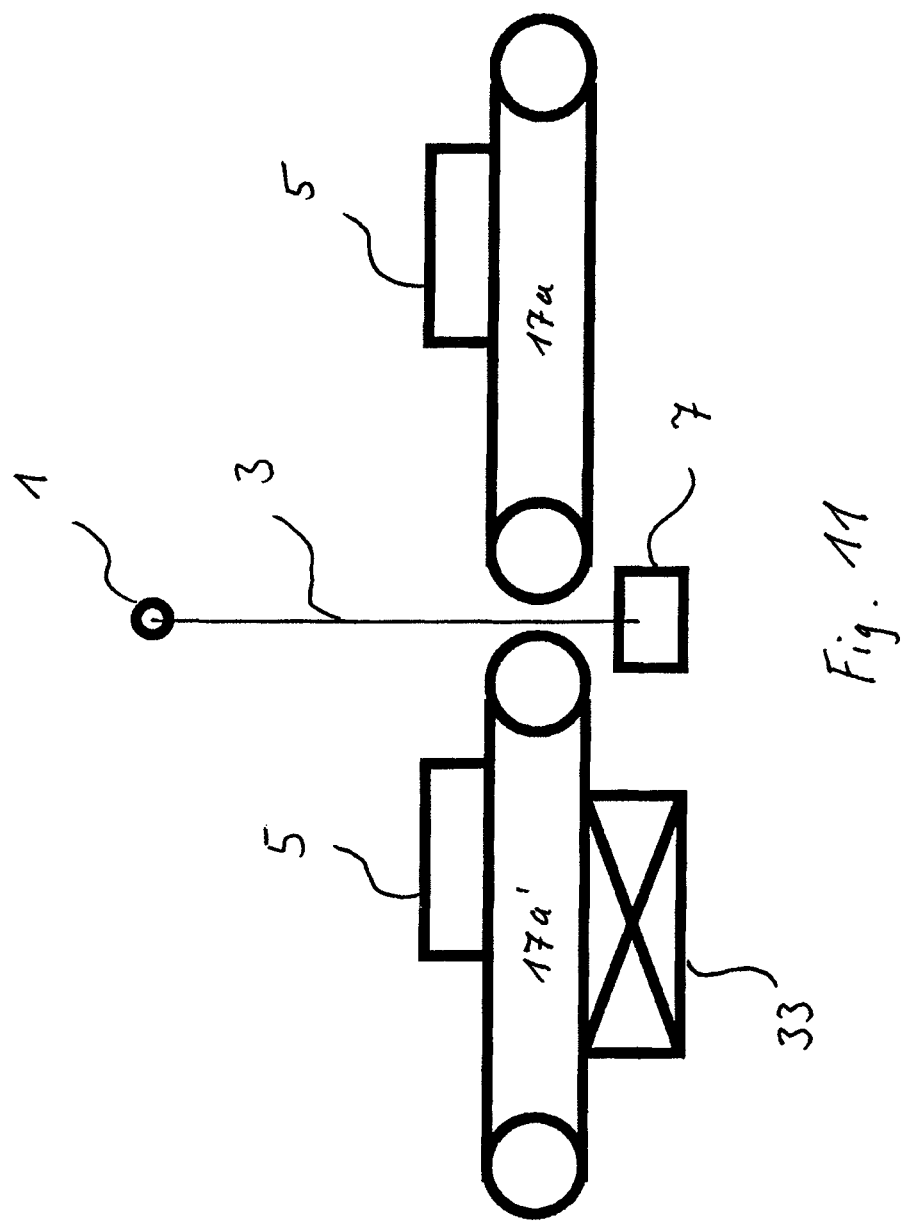

METHOD FOR X-RAYING PRODUCTS

TECHNICAL FIELD OF THE INVENTION

The invention relates to methods for X-raying products, in particular foodstuffs, as well as to devices for this purpose.

BACKGROUND OF THE INVENTION

In a production line, in particular a processing line for foodstuffs, the properties of products are examined using X-ray techniques and the examination results can be used multiple times with regard to the further processing. For example, foreign bodies may be detected, and contaminated products may be removed from the food stream by sorting. Also, various properties of the foodstuff may be identified by X-ray examination. For example, fat layers can be measured, filling levels monitored, weights determined, or a count can be made.

It is also known to predetermine the correct cutting width of food slices and to control subsequent cutting tools in such a manner that the desired slice thickness or a desired weight is precisely cut off.

To increase the production throughput, as suggested in DE102005010183B1, modern cutting devices (so-called slicers) are capable of cutting more than just one food (for example, a bar). In the process, several foodstuffs are separated simultaneously (multiple lanes), that is, in parallel.

Moreover, in the X-ray examination used in medical technology, high-precision investigations are carried out by means of three-dimensional analyses. However, the techniques used are very expensive, and they are designed specifically for immobile objects.

On the other hand, in X-ray inspection in the industrial field, the desired solutions usually have to take up little space and they have to be cost effective in order to be able to examine products that move at high speed in a product stream. Here, the goal is to be easy on the X-ray tubes to increase their lifespan, and to achieve a high degree of X-ray safety, in spite of the fact that the products of the production stream are moving continually into a room that is protected from radiation, for example, by means of bulkheads, and again out of said room.

DE102005010183B1 describes how an X-ray inspection system determines measurement data for several food bars, and how this data is used for the individual advance control of each food bar as it moves toward the next slicer. Several food bars are here X-rayed simultaneously in slices by an X-ray radiation means.

Industrial production often involves a comprehensive production line having several different process work steps, into which the X-ray inspection unit has to be integrated, without substantially changing the existing processes. Therefore, the X-ray inspection unit has to be adapted to the existing processes, particularly to the transport speed of the product stream.

In industrial production, a product stream consisting of a plurality of successive products to be X-rayed one after the other commonly comprises several lanes or several partial streams. Such so-called parallel (multiple lane) product streams are usually characterized by mutually equidistant lateral spacings (viewed transversely to the transport direction). However, in X-ray inspection or radiography (including terahertz radiation) of such a parallel product streams, problems arise that considerably affect the validity of the results of the X-ray inspection in comparison to a single-lane product stream.

In the X-raying of parallel product streams, in which the products are conveyed next to one another in the conveyance direction (also referred to herein as the transport direction)—usually on a common conveyor belt—in a plurality of several, preferably equidistant, lanes that are next to one another, the following problem causes were primarily found.

In industrial X-ray inspection, inexpensive X-ray sources are used, for cost reasons, that are also of low intensity for reasons pertaining to occupational safety. Such X-ray sources are point-shaped radiation sources, which emit, by means of screening measures, a fan-like beam bundle (in the shape of a row in cross section) (the rest of the radiation can be shadowed, for example, by a slit). Due to the point-shaped radiation source, the radiation receiver (detector) (configured with one or several rows) can be of broader design than the product stream (see FIG. 1 for example, described further below).

As soon as the radiation path from the source to the detector is no longer vertical, but forms an angle with said (central) vertical row, the radiation path from the source to the detector increases according to this angle.

Depending on the width and the height of the products to be examined in the product stream, shadowing effects result between the products that are adjacent transversely to the product stream (along the detector row), preventing an unequivocal assignment of the image pixel generated at the time of the X-raying or the irradiation to the product, because the same X-ray beam passes equally through two laterally adjacent products (see FIG. 2). In the case of shadowing effects in a parallel product stream, an unequivocal assignment of the radiation image (gray value of the pixel) to a specific product or to the product lane is no longer possible. In the sense of the invention, X-ray inspection refers to X-raying or irradiation, wherein the term X-ray beams in this connection explicitly also includes terahertz beams.

SUMMARY OF THE INVENTION

According to the invention, it has been recognized that, in the case of a parallel product stream with several products that are adjacent when viewed transversely to the transport direction (longitudinally along a detector row or rows), X-raying yields sufficient quality of the investigation results if shadowing effects between laterally adjacent products are avoided.

In order to prevent any shadowing effects, the spacing between the radiation source and the product theoretically has to be increased to infinity, which would result in near parallel X-ray radiation. However, this would increase the installation space (the installation height) of the device in an undesired and impermissible manner. The general requirement for a small installation height and a small spacing between radiation source and product is not compatible with the required avoidance of shadowing effects.

According to the invention, several products, which are adjacent transversely to the product stream (viewed transversely to the transport direction in every direction, that is laterally, on top of one another, etc.), are transferred for X-raying as a group together into a radiation-protected X-ray room, and rearranged or regrouped (with a change in the existing arrangement) in such a manner that, during the X-ray process, the X-raying is simplified and, in particular, shadowing effects are reduced or even prevented entirely.

A radiation-protected room here describes a room that does not allow radiation present in the interior to escape to the outside, or does so only in a slight, admissible manner (occupational safety).

Moreover, according to the invention, several adjacent products in the product stream are transferred in a single process automatically, without manual action on them (for example, by means of actuators, motor driven, pneumatically, by means of pressurized air, etc., and by means of a corresponding control) into the radiation-protected room and preferably released again. In this manner, radiation protection devices, such as bulkheads, curtains, ramps, etc., have to be opened and/or passed only once for several adjacent products, so that, advantageously, no time delays (for repeated opening and/or passage) occur. As a result, the hazard to the surroundings outside of the radiation-protected room can be avoided with unchanged safety (occupational safety).

In the sense of the invention, products to be investigated are products of any type, preferably of solid consistency, in particular foodstuffs, such as, for example, food bars.

The rearrangement according to the invention comprises, as explained further below, a serialization of the products and/or a change of the lane spacings, so that at least one product per X-ray process is examined, preferably in the form of rows (in slices).

In an embodiment of the invention, lanes or partial streams located laterally further toward the exterior can be pulled apart laterally for X-raying, so that the spacings between adjacent partial streams increase the further the partial streams are located to the outside, and thus the more the angle with respect to the radiation source (relative to the normal or vertical line) is increased. Depending on the product height and the spacing between product and source, the lateral spacing can here be increased advantageously in such a manner that there are also no shadowing effects between the outer lanes.

In another embodiment of the invention, the multilane product stream for X-raying the products is reduced mechanically from a number of n lanes to a number of m lanes, so that only groups having sufficiently spaced products (m>1) or an individual product (m=1) are moved through the X-ray beam (X-ray process). Here, the regrouping preferably occurs in such a manner that the resulting product stream of m lanes is centered toward the source or toward the central vertical line of the beam. In the case of groups of several products (multilane or parallel X-raying) as well, this prevents products or lanes form being located further toward the outside, which could be exposed to stronger shadowing effects, due to the greater lateral spacing with respect to the source.

This reduction of the number of lanes (from n to m) can be understood as a serialization, wherein, in the sense of the invention, serializing refers not only to a scanning of an individual product, but also to the scanning of several adjacent products, for example, two adjacent products in a group (transversely to the product stream), as long as the number of lanes during the X-raying is reduced in comparison to the number of lanes previously present.

In the case of parallel X-raying, the products preferably have—viewed in the direction of the product stream—identical dimensions (length), and they are moved transversely to the product stream without mutual offset, that is, head to head or front flank to front flank, through the X-ray beam. However, it is also conceivable to move products that have different lengths and/or a different offset through the X-ray beam. The resulting transitions (change in the number of simultaneously X-rayed products) can be detected, for example, on the basis of abrupt changes in the values (absorption values) in the detector.

In another embodiment of the invention, for the X-raying, the lanes of the multilane product stream, which are provided in parallel, are each moved forward separately, for example, at a different speed and/or in different steps, and conveyed through the, for example, stationary, fan-shaped X-ray beam. For this embodiment as well, it is advantageous to avoid the shadowing of adjacent products without any decrease in the product stream speed and without exceeding an undesired or even impermissible installation height for the X-ray inspection device.

In a preferred embodiment of the invention, the products (and/or lanes), after the X-raying, in particular before further processing, are arranged in the X-ray room in such a manner that their relative position to one another and/or relative to the product stream correspond(s) to the position before the X-raying. As a result, the X-ray inspection can take place advantageously without influencing the required arrangement for a further processing. In a particularly preferred design of the invention, the entire X-ray inspection also takes place laterally in a manner that makes it possible to avoid or minimize delay with regard to the product stream movement and the previous and/or subsequent work steps. This can be achieved, for example, by a higher conveyor belt speed of the individual belts or the lane in the X-ray room with respect to the conveyance speed of the product stream outside of the X-ray room.

As a result, it is possible, advantageously, to construct not only production rows, but also to retrofit production rows, without having to take into consideration the X-ray device as in the (previous) control and movement of the product stream. This allows an integration of the X-ray inspection unit or device in a comprehensive production line that has several different process work steps, without substantially changing the existing processes.

Naturally, it is conceivable to design the X-ray source and/or the detector not only in a stationary design, but also so it can be moved at an angle that is greater than zero, preferably transversely to and/or parallel to the production stream. Besides allowing an increase in the conveyance speed and/or a change in the lane guidance (individual belts), this also makes it possible to achieve a change in the arrangement of the products for the X-raying and/or to increase the X-raying speed.

In another embodiment of the invention, before, during or after the X-raying, the weight of individual products adjacent transversely to and/or in the transport direction and/or their total weight can be determined by means of at least one weighing cell or scale. The determined weight can be used advantageously for various inspection tasks, such as, for example, for a density determination/monitoring, a fat analysis, or a slice width determination of food slices that have a precise predetermined weight.

Even if a determination of the weight by means of an expensive evaluation of the values obtained by X-ray inspection is possible, the determination of the weight of individual products or the total weight of a product group (for parallel weighing) by means of a scale or weighing cell is more rapid and more precise.

Given that the weight of a product is known, and the individual absorption values obtained row-wise (constant thickness) (proportional to the density and thickness/width/height) of a product are also known, it is possible to determine the weight for an individual slice in a simple manner. The thickness of such a scanned slice here is dependent on factors including the width of the detector cell or rows. This data can be used, for example, for an above-mentioned slice width determination for each lane, in order to control a slicer accordingly.

The at least one weighing cell or the at least one scale is here integrated preferably in the X-ray direction, in particular in the radiation-protected room (X-ray room). This makes it possible advantageously to dispense with a housing and with wind protection for the scale or the weighing cell, since the interior space of the X-ray inspection device is provided with the radiation protection measures, which reliably prevent not only the exit of X-ray radiation, but also the entry of wind (which is disadvantageous for weighing).

Naturally, the above-mentioned embodiments of the invention can be combined in any desired manner with each other, allowing a plurality of mixed forms.

These and other advantages and features of the invention will be apparent from the following description of illustrative embodiments, considered along with the accompanying drawings.

BRIEF DESCRIPTION OF THE DRAWINGS

In the drawings:

FIG. 3 shows a top view of a first embodiment of a section of a production row with an X-ray device according to FIG. 1;

FIG. 4a shows a top view of a second embodiment of an X-ray device according to FIG. 1;

FIG. 4b shows a top view of a fourth embodiment of an X-ray device according to FIG. 1;

FIG. 4c shows a top view of a third embodiment of an X-ray device according to FIG. 1;

FIG. 5 shows a top view of a second embodiment of a section of a production line with an X-ray device according to FIG. 1;

FIG. 6b shows a cross-sectional view along an X-ray beam 3 in FIG. 6a;

FIG. 7b shows a top view of a fourth embodiment of a section of a production line with an X-ray device according to FIG. 1;

FIG. 9 shows a top view of a fifth embodiment of a section of a production line with an X-ray device according to FIG. 1 with a common weighing belt;

FIG. 10 shows a top view of a sixth embodiment of a section of a production line according to FIG. 9 with a scale arranged after an X-ray inspection unit; and FIG. 11 shows a diagrammatic side view of FIG. 10.

DESCRIPTION OF ILLUSTRATIVE EMBODIMENTS

Figure 1:
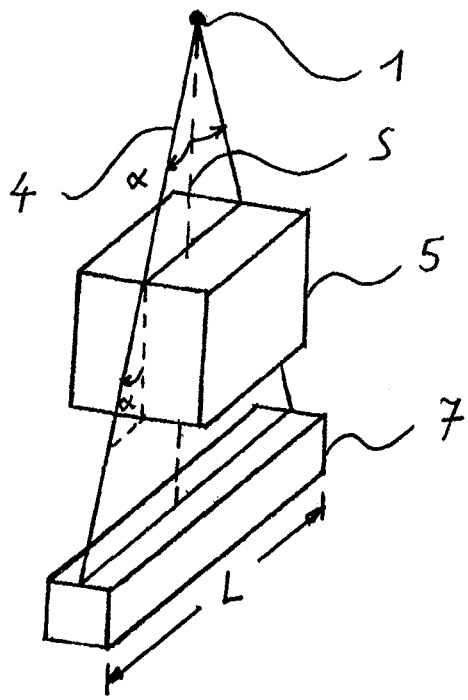
FIG. 1 shows a perspective view of a diagrammatically represented X-ray device.

FIG. 1 is a diagrammatic representation of an instantaneous view of the process of X-raying a product 5. A fan-shaped beam 3 originating from a radiation source 1, in particular an X-ray source, passes through the product 5, so that, on the opposite side, the row-shaped radiation that is not absorbed by the product 5 impinges on a detector 7 or the detector row or rows thereof. According to the invention, detector 7 and source 1 are arranged at an angle that is greater than zero, preferably transversely to the product stream or to the transport direction.

The required length L (hereafter also referred to as the detector width) of the detector 7 varies according to the width and the height of the products 5, as well as the spacing from source 1 to the product 5, and the spacing from detector 7 to the product. As can be seen in FIG. 1, this is due to the angle $\alpha$ formed by a lateral beam 4, which still barely penetrates the product 5 in its outermost area (for example, the upper outer edge), and a vertical line S (starting from source 1 and perpendicularly to the detector 7).

Figure 2:
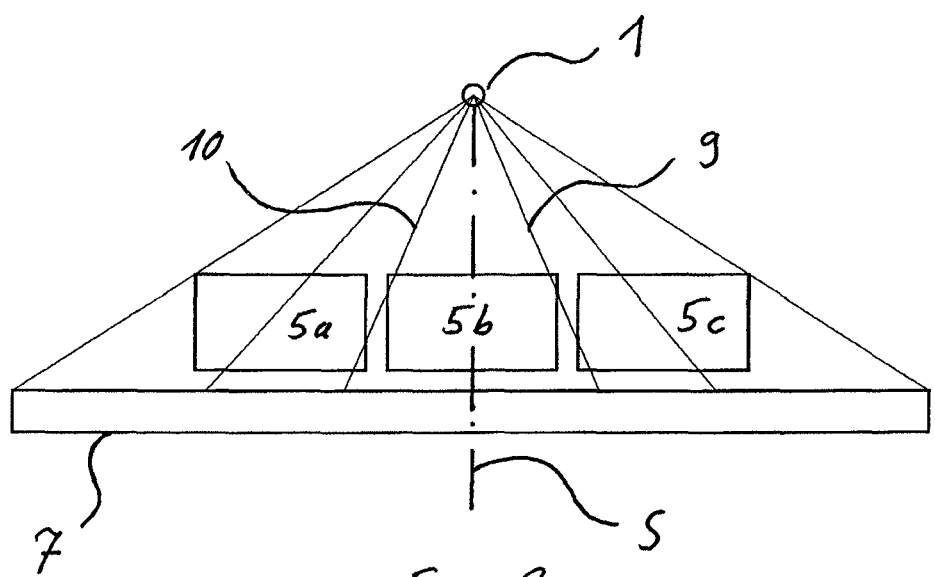
FIG. 2 shows a cross-sectional view of several products during a scan with an X-ray device according to FIG. 1.

As can be seen in FIG. 2, it is precisely in the area of the beams with larger angle $\alpha$ that shadowing effects occur on an adjacent product. Moreover, a beam 9, which passes through the outermost areas of the product 5b, moreover also passes through the adjacent product 5c (in the drawing, the left bottom outer edge thereof), before it impinges on the detector 7. The same applies to the beam 10, except that this beam 10 passes through the left outermost area of the product 5b, and consequently, before impinging on the detector 7, it still passes through the lower right outer edge of product 5a. However, such shadowing effects, which increase for products or lanes located on the outside, bias the measured value in the detector in such a manner that an assignment to a lane and/or to a product 5 is no longer possible. Differences in the path length through the product due to different angles, on the other hand, are negligible, or they are resolved by appropriate correction methods during the evaluation.

The first embodiment of a section of a product line, which is represented in FIG. 3, with an X-ray device 19 according to FIG. 1 consisting of a source 1 and a detector 7, shows a serialization according to the invention of the products 5 or 5a, 5b, 5c, 5d. In the process, the products 5a, 5b, 5c, 5d, which are located laterally, equidistantly and head to head or front flank to front flank next to one another in the product stream on a conveyor belt 11, are transferred together, in parallel, into a radiation-protected room or an X-ray room 13, in particular a radiography room, then pass through the opening and closing of a radiation protection device, for example, an inlet bulkhead 15.

After the joint introduction of the products 5a, 5b, 5c, 5d as a group into the X-ray room, and after the closing of the inlet bulkhead 15, the product lanes 17 or 17a, 17b, 17c, 17d, which are made available in parallel, are each moved separately individually forward and conveyed individually through the X-ray beam 3. This reliably prevents shadowing effects.

Now, all the products 5a, 5b, 5c, 5d of the individual lanes 17a, 17b, 17c, 17d are moved forward temporally one after the other until all the products present in the X-ray room 13 have been X-rayed. In the process, it is preferable for all the individual lanes 17a, 17b, 17c, 17d to move forward simultaneously. One only must ensure that, at all times, rays pass through only one product The transport speed in the interior of the X-ray inspection device or in the X-ray room 13 can be substantially higher than that required of the production stream outside of the X-ray room 13, since, in the X-ray room 13 at least one separate transport system is present, for example, in the form of separately controllable individual lanes (individual straps) or individual belts 17a, 17b, 17c, 17d.

Figure 8:
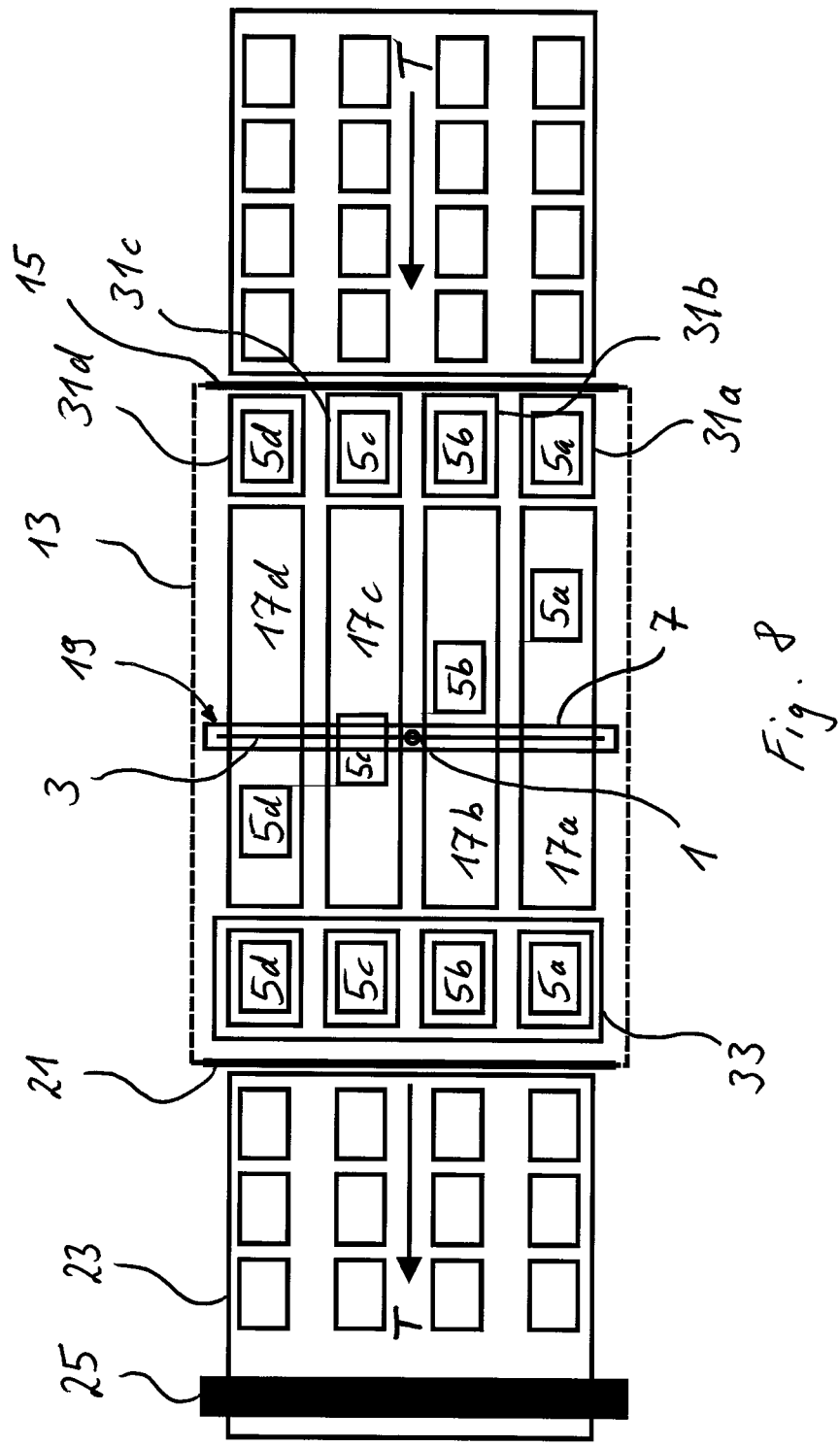
FIG. 8 shows a top view of the first embodiment of a section according to FIG. 3 with a scale arranged before and/or after the X-ray unit.

As can be seen in FIG. 8, if the products 5 are of equal length, but also if the products 5 are of different lengths, the subsequent product can be moved with its front edge or flank preferably so close to the rear flank of the previous product 5a to 5b, 5b to 5c, 5c to 5d, that almost no gap occurs, and no processing time is wasted.

After all the individual products 5 or 5a, 5b, 5c, 5d have passed by the X-ray beam 3 on their respective lanes 17a, 17b, 17c, 17d, they can, depending on the required further processing, remain arranged longitudinally offset (serially) with respect to each other. Naturally, it is also conceivable to move the products 5a, 5b, 5c, 5d after they have passed by the X-ray beam 3, by means of appropriate devices (individual conveyor belts, mechanical stoppers, etc.), into a mutually parallel position (head to head next to each other). This is particularly advantageous, provided a subsequent processing step allows a parallel processing or even requires it. For example, in this manner, in a downstream cutting process (slicer), all the products or lanes can then be cut or separated in parallel.

In a special embodiment as represented, for example, in FIGS. 8 and 9, the already X-rayed products 5 are moved out of the X-ray room 13 in parallel. This can occur, preferably, in the same cycle as the feeding of new products 5 into the X-ray room 13, since during both processes (introduction and removal), it may be required to switch off the source 1 and thus the X-ray for safety reasons.

The introduction of the products 5 into the X-ray room 13 and/or their removal from the X-ray room can occur either serially or also in parallel. The serialization according to the invention for the X-ray inspection and preferably the subsequent parallelization are preferably carried out in the X-ray room 13, because this results in advantages during the opening and/or closing of the inlet bulkhead 15 and the outlet bulkhead 21 (small number of opening/closing processes, shorter opening times, etc.). Naturally, it is also conceivable to carry out the serialization and/or parallelization outside of the X-ray room.

As can be seen in FIGS. 4a-4c, instead of a stationary X-ray device 19, as shown in FIG. 1, with a stationary source 1 and a stationary detector 7, other embodiments of X-ray devices 19 or X-ray units are also possible. Thus, FIG. 4a shows a second embodiment of an X-ray device 19 with a source 1 that can be moved over the scanning width, while the detector 7 has a stationary design. In this case, the detector 7 has a length L over the entire scanning width or production stream width, while the spread of the beam 3 of the moving source 1 covers only a single product in its lane width.

On the other hand, FIG. 4c shows a third embodiment of an X-ray device 19 with a detector 7 that can be moved over the scanning width, while the source 1 is designed so it is stationary and the fan-shaped X-ray beam 3 covers the entire scanning width or production stream width, and the detector width covers only the (lane) width of a product 5. FIG. 4b finally shows a fourth embodiment of an X-ray device 19, in which both source 1 and detector 7 are designed to be movable, in order to cover the entire width of the X-raying (scan). In this case, both the beam 3 and the detector width opposite the entire scanning width have small dimensions compared to the total scanning width, since here only one product has to be X-rayed centrally in each case, for example.

In this manner, the X-ray beam width and/or beam detector length (in each case transversely to the product stream or to the product conveyance direction) can be designed to be very small and cost effective. The required X-ray power is moreover lower than in the case of a stationary first embodiment, as a result of which the lifespan of the components is increased. Consequently, advantageously smaller, more cost effective radiation protection measures can be used.

The above explained method of serialization can also be applied in a second embodiment of the invention to groups of at least two products 5. As can be seen in FIG. 5, laterally adjacent products 5a, 5b, 5c, 5d, 5e, 5f can be combined, for example, in groups of two (the group number is always smaller than the number of the laterally adjacent products) 5a, 5b; 5c, 5d; 5e, 5f. In contrast to the first embodiment, in this second embodiment, groups of at least two products 5a, 5b; 5c, 5d; 5e, 5f are provided in parallel in product lanes 17 or 17a, 17b and 17c, so that each group is moved forward separately individually and is conveyed individually through the X-ray beam 3. If the spacing, particularly in the outer lanes 17a and 17c, between the products 5a, 5b and 5e, 5f is not sufficient to prevent shadowing effects, the respective spacing can be increased, as described below in a third embodiment, for example. However, it is also conceivable, as described above, to configure at least the source 1 so it can be moved transversely or at an inclination with respect to the product stream in order to prevent shadowing effects. Instead of arranging directly adjacent products to form groups, it is, however, also conceivable to combine mutually separated products to form a group (for example, 5a, 5d; 5b, 5e and 5c, 5f).

Figure 6A:
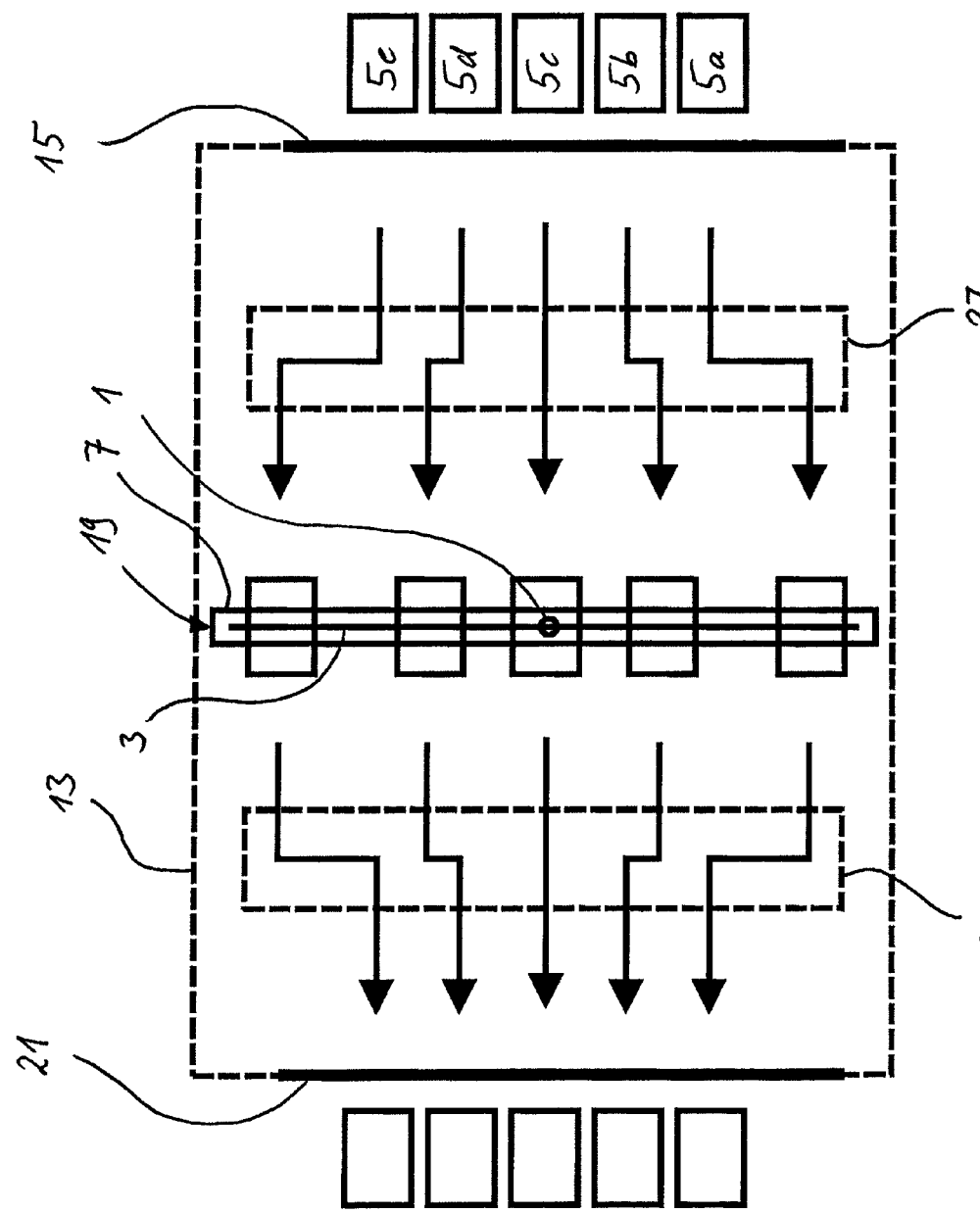
FIG. 6a shows a top view of a third embodiment of a section of a production line with an X-ray device according to FIG. 1.

In the third embodiment of the invention represented in FIG. 6a, the interfering shadowing is avoided by pulling the lanes laterally apart. This pulling apart or spreading of the lanes can be achieved by means of suitable mechanical devices 27, such as, for example, mechanical (side) guides, individual belts with greater spacing, etc. Here, outer lanes and thus products 5a (to 5b) and 5e (to 5d) are pulled apart more strongly than the products 5b and 5d which are being conveyed further toward the interior, in order to generate the larger spacings in the outer area between the products 5a to 5b and products 5d to 5e in this manner as shown in FIG. 6b, and to prevent shadowing effects.

As can be seen in FIG. 6b, none of the beams of the fan-like X-ray beam passes through more than one product 5a, 5b, 5c, 5d or 5e on its way to the detector 7. However, owing to the larger angle α, this embodiment requires a correspondingly larger length L of the detector 7. If, for the further processing behind the X-ray inspection, the original lateral product spacing of the product line is needed again, then the products 5 can again be newly oriented by a second mechanical device 29. The second mechanical device 29 can here be configured analogously to the first mechanical device 27 in the corresponding reversal (compacting instead of spreading).

Figure 7A:
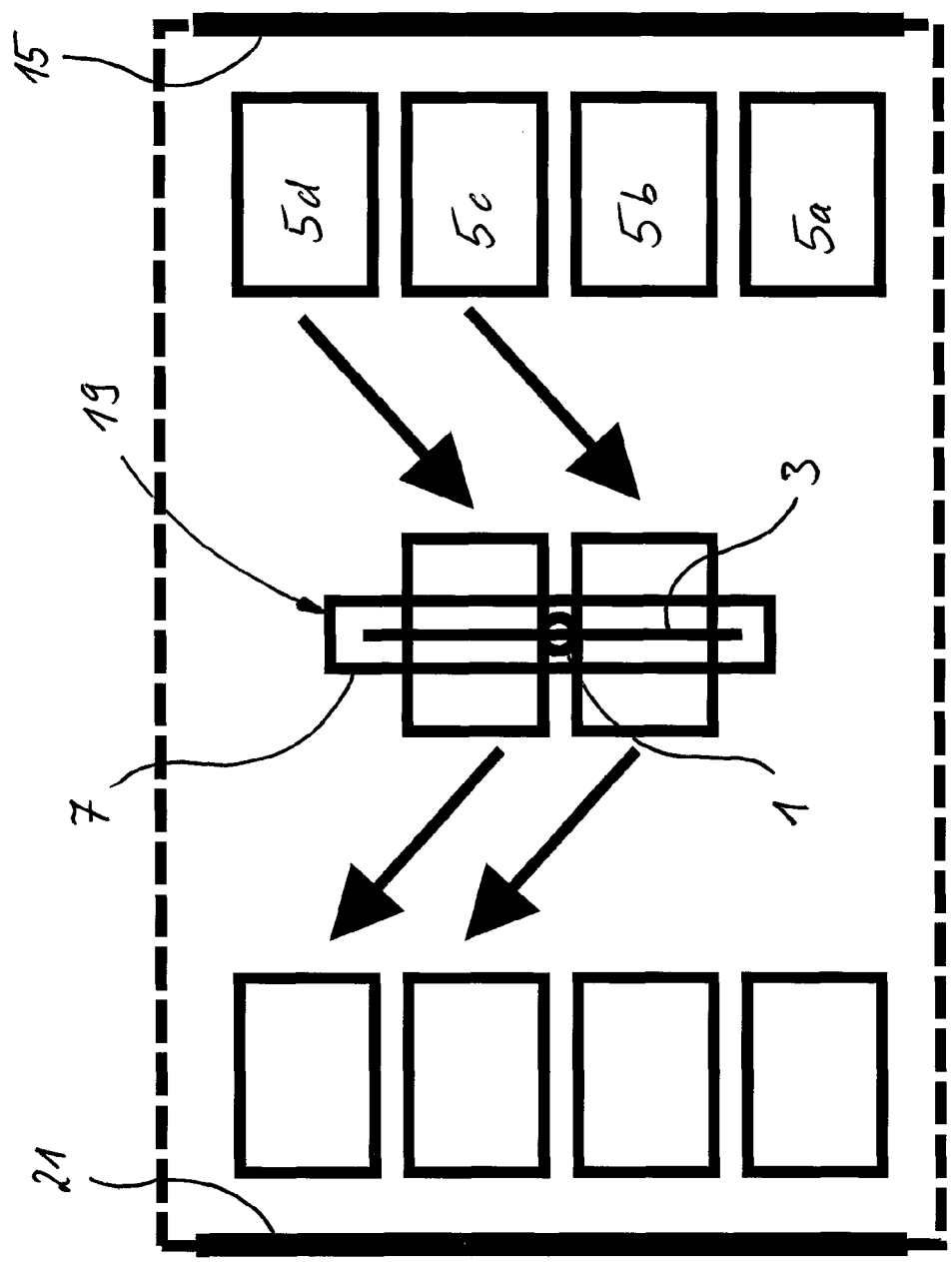
FIG. 7a shows a top view of a fourth embodiment of a section of a production line with an X-ray device according to FIG. 1.

According to the fourth embodiment of the invention, which is represented in FIGS. 7a and 7b, it is also conceivable to move laterally adjacent products 5a, 5b, 5c, 5d individually or in groups, for example, in groups of two, one after the other through the X-ray beam 3 or the X-ray device 19. In this manner, in contrast to the above-explained embodiment, for example, first the products 5c and 5d (along the arrows in FIG. 7a) are X-rayed and only thereafter the products 5a and 5b (along the arrows in FIG. 7b) are X-rayed. Such a regrouping or repositioning of products occurs by (mechanical) reduction of the number of lanes in the X-ray room, so that the product stream is investigated sequentially (in temporally successive steps). The regrouping and X-raying occur preferably at a higher speed than the (required) transport speed of the product stream, so that this product speed remains uninfluenced by the X-ray inspection. Here, it is advantageous for both the source 1 and also the detector 7 to be in a stationary arrangement.

In a preferred embodiment, here one prevents that a radiation protection device, in particular an X-ray bulkhead 15, has to be opened and/or closed again before each individual product 5 or before each group of products 5a, 5b; 5c, 5d is introduced into the X-ray room 13 or leaves said room. This becomes possible if all the adjacent products 5a, 5b, 5c, 5d of the parallel product stream—as represented in FIGS. 7a and 7b—are transferred in parallel as a group of products 5a, 5b, 5c, 5d into the X-ray room 13. Here, the inlet bulkhead 15 and any outlet bulkhead 21 present in each case have be opened and closed only once.

In this manner, it is advantageously possible to carry out a near parallel X-ray inspection toward the outside at full transport speed of the production line or the production stream. In addition, this makes it possible to avoid expensive mechanical devices, which increase the installation space and generate costs.

According to the invention, it is possible, in any design, for this section of a production line with an X-ray device 19 to be provided additionally with at least one scale or at least one weighing cell. This at least one scale is used for determining the weight of the individual products and/or the total weight of a group of adjacent products 5a, 5b, 5c, 5d transferred together into the X-ray room 13. The weight is required for various inspection tasks, such as a density determination/monitoring (including a fat analysis) (calculated from volume and weight, for example), a slice width determination of food sliced that has a predetermined precise weight, etc.

As represented in FIG. 8, the scale can be arranged before and/or after the X-ray unit 19, and is preferably integrated in the X-ray inspection device or in the X-ray room 13. The integration here can involve the data technological integration in a common control unit, in addition to and/or instead of the arrangement in a common housing.

The section of a production line represented in FIG. 8 substantially corresponds to the first above-explained embodiment of a section according to FIG. 3. However, in FIG. 8, the representation additionally shows how and in which position at least one scale 33; 31a, 31b, 31c, 31d can be arranged, preferably in the X-ray room 13. Thus, the weighing of products 5a, 5b, 5c, 5d, which have already passed through the inlet bulkhead 15, is protected from wind (closed bulkheads 15 and 21) on separate individual scales 31a, 31b, 31c, 31d or individual weighing cells with their own conveyance means, in particular conveyor belts.

Instead of the individual scales 31a, 31b, 31c, 31d, it is also conceivable to use a common weighing platform. Said platform is loaded first with the totality of the products 5a, 5b, 5c, 5d of all the lanes (total load). Gradually, one after the other, the products 5a, 5b, 5c, 5d of the individual lanes are now transported from the weighing platform downward to the X-ray inspection device 19. The weight difference produced as the weighing platform is lowered is determined by subtracting the weight values before and after the downward transport.

The separation of (previous and/or subsequent) scales 33; 31a, 31b, 31c, 31d and the individual conveyor belts 17a, 17b, 17c, 17d required for the serialization represent an advantageous embodiment of the invention, since, as a result, the mechanical effects of the individual conveyor belts 17a, 17b, 17c, 17d on the weighing process can be avoided.

After the X-ray inspection unit or device 19, it is again possible to arrange, separately from the individual conveyor belts 17a, 17b, 17c, 17d, a weighing scale 33 which is applied to all the lanes or uses a common weighing platform for all the lanes that supports all the individual (parallel) weighing conveyor belts (or groups thereof).

Since the products 5a, 5b, 5c, 5d arrive one after the other at the overall scale 33, it is possible to determine not only the total weight of all the products 5a, 5b, 5c, 5d, but also the change in the weight, particularly by difference weighing (also referred to as subtraction weighing).

According to the solution represented in FIG. 9, the structure of the overall arrangement can also be simplified by having the parallel conveyor belts 17a, 17b, 17c, 17d, which transport the products 5a, 5b, 5c, 5d through the X-ray beam 3, be themselves designed as weighing belts, that is, the belts are connected to the weighing platform(s), and supported by the latter as a preload.

By tolerating a limited analysis speed, it is also naturally possible to use, instead of the parallel weighing belts and/or individual scales, a large common weighing belt or weighing platform that is supported on a single weighing cell. As a result, the number of interferences (balancing) with the measurement technology would be avoided advantageously. However, for the serialization/parallelization it is then necessary to use at least one set of parallel individual transport devices, which can be arranged before or after the weighing belt.

From the point of view of the weighing technology, it is advantageous to position a so-called inlet belt 39a, 39b, 39c and 39d before an individual belt 17a, 17b, 17c, 17d, as represented in FIG. 9, which inlet belts transport at exactly the same speed as the respective individual belts 17a, 17b, 17c, 17d. In this manner, transfer problems (impacts that can excite oscillations of the scale structure) between the inlet belts 39a, 39b, 39c and 39d and the individual belts 17a, 17b, 17c, 17d can be avoided. An individual belt 17a, 17b, 17c, 17d can preferably always convey at constant speed and without interruption. As a result, a continuous product stream would be achieved with the best possible weighing precision.

After the X-raying, the subsequent parallelization occurs either by means of four parallel individual belts 45 or by means of mechanical stoppers 43 or other devices that produce the same parallelizing effect. In the process, the position and setting (rotation, in any direction) of the products, except for the parallelization, are not changed disadvantageously.

As a result of a subsequent parallelization, it is possible, in the different embodiments, to simplify a subsequent processing, particularly an exact definition of cutting positions of subsequent processing devices, for example, slicers.

According to the sixth embodiment of the invention, which is represented in FIGS. 10 and 11, the individual belts 17a, 17b, 17c, 17d can end in the longitudinal direction immediately before the X-ray inspection unit 19 (and thus before the beam 3). Immediately after the X-ray inspection unit 19 or the beam 3, the belts or straps (lanes) 17a', 17b', 17c', 17d' then follow with lane accuracy and in each case identical speed. Thus, the pairs 17a, 17a'; 17b, 17b'; 17c, 17c' and 17d, 17d', in terms of their function, replace the continuous individual belts 17a, 17b, 17c, 17d represented in the previous embodiments, except that, in this embodiment, the beam 3 (next to a product 5a, 5b, 5c, 5d) does not have to pass through a belt 17a, 17b, 17c, 17d on its way from source 1 to the detector 7. In this way, interfering, in particular inconstant, influences (soiling, material deviations, seams, etc.) of the belts 17a, 17b, 17c, 17d on an X-ray process can be advantageously avoided.

The slit between the respective belt pairs 17a, 17a'; 17b, 17b'; 17c, 17c' and 17d, 17d' is here so small that the conveyance of the products 5a, 5b, 5c, 5d is not influenced in an interfering manner. In the embodiment represented in FIGS. 10 and 11, the scale is arranged preferably after the X-ray inspection device 19 and preferably as an overall scale 33.

In a preferred embodiment with a downstream scale, it is also conceivable, in the user-defined embodiments of the invention, that a weighing of the last product 5a to be weighed from group 5a, 5b, 5c, 5d will trigger, on the basis of control technology, additional further actions, such as switching off the X-ray source 1, opening the bulkhead 15, 21, the introduction of the next group of adjacent products 5a, 5b, 5c, 5d, etc.

All the control technological processes of any design of the invention, such as the takeover of the products, the inlet/outlet of the products into or out of the radiation-protected room, the opening/closing of the bulkhead, the control of the transport devices (straps, belts, stoppers, etc.), the control of the X-ray direction, the control of the scale(s), the rearrangement of the products, the data processing, etc., are taken over by a known control and/or evaluation device.

Naturally, the characteristics of the various embodiment examples that have been explained as examples can be combined with each other.

The particular advantages of the invention to be indicated are, besides a short and flat installation space, the small width required, which is only minimally larger than the product stream, the high throughput, as well as an ideal adaptation to an existing product stream or a production line in the sense of a black box solution (representing to the outside no effect at all and allowing an apparently purely parallel operation within the entire production line).

As used herein, whether in the above description or the following claims, the terms "comprising," "including," "carrying," "having," "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention.

LIST OF REFERENCE NUMERALS

1 Radiation source
3 Fan-like X-ray beam
4 Outermost beam
5 Product
5a Product
5b Product
5c Product
5d Product
7 Detector
9 Right outer beam for product 5b
10 Left outer beam for product 5b
11 Supply belt
13 X-ray room
15 Bulkhead inlet
17 Belt or product lane
17a Individual belt (lane) or strap
17b Individual belt (lane) or strap
17c Individual belt (lane) or strap
17d Individual belt (lane) or strap
19 X-ray unit or X-ray device
21 Bulkhead outlet
23 Discharge belt
25 Slicer station
27 Mechanical device
29 Mechanical device
31a Scale
31b Scale
31c Scale
31d Scale
33 Overall scale
35 Weighing belt
37 Weighing cell
39 Inlet belt
41 Common weighing platform with several (transport) lanes
43 Stopper
45 Discharge station
T Transport direction
S Vertical line from source 1 to product 5
α Angle between beam 4 and vertical line S

The invention claimed is:

1. A method for use with X-ray inspection of products of a product stream in which the products are conveyed in a number n lanes parallel to each other in a conveyance direction, the method including:
   (a) transferring two or more products as a group together into a radiation-protected X-ray room, the two or more products comprising a respective product from two or more of the n lanes and being spaced apart transversely to the conveyance direction; and
   (b) while the two or more products are in the X-ray room, rearranging the two or more products for an X-ray inspection process in the X-ray room, the rearranging serving to change the positions of the two or more products relative to each other in the X-ray room and to increase a spacing between the two or more products, the spacing increase being transverse to the conveyance direction, in the conveyance direction, or both transverse to and in the conveyance direction.

2. The method of claim 1 wherein rearranging the two or more products includes serializing the two or more products before or during the X-ray inspection process in the X-ray room so that the two or more products are moved in the conveyance direction during the X-ray inspection process in no more than a number m lanes traversing a X-ray beam of the X-ray inspection process, the number m being less than the number n and greater than or equal to 1.

3. The method of claim 1 wherein rearranging the two or more products includes regrouping the two or more products in no more than a number m lanes in a direction of a central vertical line S of a X-ray beam of the X-ray inspection process, wherein the number m is less than the number n and greater than or equal to 1.

4. The method of claim 1 further including, after the X-ray inspection process is applied to the two or more products, arranging the two or more products within the X-ray room in such a manner that the position of the two or more products with respect to each other corresponds to a position before the two or more products were rearranged for the X-ray inspection process.

5. The method of claim 1 wherein the X-ray inspection process includes moving a radiation source or a detector at an angle greater than zero or parallel to the conveyance direction.

6. The method of claim 1 wherein the X-ray inspection process is performed by means of an immobile radiation source or an immobile detector.

7. The method of claim 1 further including, during or after the X-ray inspection process is applied to the two or more products, determining the weight of each of the two or more products or the total weight of the two or more products with at least one scale.

8. The method of claim 1 wherein the two or more products include at least one central product and a first outside product to a first lateral side of the at least one central product, and further including increasing a spacing transverse to the conveyance direction between the first outside product and a next adjacent product to the first outside product.

9. The method of claim 8 wherein the two or more products include a second outside product to a second lateral side of the at least one central product, and further including increasing a spacing transverse to the conveyance direction between the second outside product and a next adjacent product to the second outside product.

10. A device for X-ray inspection of products of a product stream in which the products are conveyed in a number n lanes parallel to each other in a conveyance direction, the device including:
 (a) an X-ray room which is radiation-protected with respect to the surroundings thereof, the X-ray room having associated there with an X-ray source and an X-ray detector;
 (b) an inlet of the X-ray room adapted to receive there through into the X-ray room two or more products together as a group, the two or more products comprising a respective product from two of more of the n lanes and being spaced apart transversely to the conveyance direction; and
 (c) a rearranging device within the X-ray room for rearranging the two or more products for an X-ray inspection process in the X-ray room, the rearranging being operable to change the position of the two or more products relative to each other in the X-ray room and to increase a spacing between the two or more products, the spacing increase being transverse to the conveyance direction, in the conveyance direction, or both transverse to and in the conveyance direction.

11. The device of claim 10 wherein the products conveyed in the n lanes are in a production line which is uninfluenced by operation of the device.

12. The device of claim 11 wherein the production line is a foodstuff production line.

13. The device of claim 10 wherein the rearranging performed by the rearranging device serializes the two or more products before or during the X-ray inspection process so that the two or more products are moved in the conveyance direction during the X-ray inspection process in no more than a number m lanes traversing a X-ray beam of the X-ray inspection process, the number m being less than the number n and greater than or equal to 1.

14. The device of claim 10 wherein the rearranging performed by the rearranging device regroups the two or more products in no more than a number m lanes in a direction of a central vertical line S of a X-ray beam of the X-ray inspection process, wherein the number m is less than the number n and greater than or equal to 1.

15. The device of claim 10 wherein the rearranging device is operable to, after the X-ray inspection process is applied to the two or more products, place the two or more products in a position with respect to each other in which the two or more products were transferred into the X-ray room.

16. The device of claim 10 further including at least one scale operable to, during or after the X-ray inspection process is applied to the two or more products, determine the weight of each of the two or more products in the X-ray room or the total weight of the two or more products in the X-ray room.

17. The device of claim 10 wherein the two or more products include at least one central product and a first outside product to a first lateral side of the at least one central product, and wherein the rearranging device is operable to increase a spacing transverse to the conveyance direction between the first outside product and a next adjacent product to the first outside product.

18. The device of claim 17 wherein the two or more products include a second outside product to a second lateral side of the at least one central product opposite the first lateral side, and wherein the rearranging device is operable to increase a spacing transverse to the conveyance direction between the second outside product and a next adjacent product to the second outside product.

* * * * *